(12) United States Patent
Higuchi et al.

(10) Patent No.: US 9,186,058 B2
(45) Date of Patent: Nov. 17, 2015

(54) IMAGE PROCESSING APPARATUS

(71) Applicant: NIDEK CO., LTD., Aichi (JP)

(72) Inventors: Yukihiro Higuchi, Toyota (JP); Yuji Murase, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 122 days.

(21) Appl. No.: 14/161,831

(22) Filed: Jan. 23, 2014

(65) Prior Publication Data
US 2014/0204342 A1    Jul. 24, 2014

(30) Foreign Application Priority Data

Jan. 23, 2013  (JP) ................ 2013-010442

(51) Int. Cl.
*A61B 3/10* (2006.01)
*A61B 3/14* (2006.01)

(52) U.S. Cl.
CPC ............. *A61B 3/102* (2013.01); *A61B 3/1025* (2013.01); *A61B 3/14* (2013.01)

(58) Field of Classification Search
CPC ........ A61B 3/102; A61B 3/1025; A61B 3/12; A61B 3/1233; A61B 3/14; A61B 3/145
USPC ........................... 351/205, 206, 208, 210, 246
See application file for complete search history.

(56) References Cited

U.S. PATENT DOCUMENTS

| 8,836,951 B2 * | 9/2014 | Yuasa ........................... 356/497 |
| 2008/0024721 A1 | 1/2008 | Ueno et al. |
| 2013/0002711 A1 * | 1/2013 | Sakagawa ..................... 345/619 |

FOREIGN PATENT DOCUMENTS

JP     2008-29467 A     2/2008

OTHER PUBLICATIONS

Search Report dated Jul. 2, 2014 issued by the European Patent Office in corresponding European Patent Application No. 14152050.2.

* cited by examiner

*Primary Examiner* — Huy K Mai
(74) *Attorney, Agent, or Firm* — Sughrue Mion, PLLC

(57) ABSTRACT

An image processing apparatus configured to process a tomographic image of an object to be examined, includes: a processor; and memory storing computer readable instructions, when executed by the processor, causing the image processing apparatus to: set a reference line, which is used as a reference for setting a cross sectional position, on a front image of the object, the cross sectional position being one of a position where a two-dimensional tomographic image is acquired from three-dimensional data of the object, and a position where measurement light for generating a tomographic image is scanned; and set the cross sectional position having a predetermined angle as an angle relative to the set reference line.

17 Claims, 10 Drawing Sheets

FIG. 4

DESIGNATED PART PHOTOGRAPHING CONDITION SETTING SCREEN ~15

< REFERENCE LINE SETTING METHOD >
- ● PAPILLA AND MACULA AUTOMATIC SETTING
- ○ DIRECT MANUAL SETTING
- ○ PASSING POINT MANUAL SETTING

< RELATIVE ANGLE >
- ● PERPENDICULAR
- ○ ARBITRARY DESIGNATION [     ] DEGREES

< CROSS SECTIONAL POSITION SETTING METHOD >
- ● MANUAL
- ○ NUMBER DESIGNATION [     ]
- ○ SPACE DESIGNATION [     ] mm

< REFERENCE LINE PHOTOGRAPHING >
- ○ YES
- ● NO

FIG. 5

BLOOD VESSEL PHOTOGRAPHING CONDITION SETTING SCREEN ~16

< RELATIVE ANGLE >
- ● PERPENDICULAR
- ○ ARBITRARY DESIGNATION [     ] DEGREES

< CROSS SECTIONAL POSITION SETTING METHOD >
- ● MANUAL
- ○ NUMBER DESIGNATION [     ]
- ○ SPACE DESIGNATION [     ] mm

< DISPLAY METHOD >
- ○ MOVING IMAGE
- ● STILL IMAGE

IMAGE PROCESSING APPARATUS

CROSS REFERENCE TO RELATED APPLICATION

This application is based upon and claims the benefit of priority of Japanese Patent Application No. 2013-010442 filed on Jan. 23, 2013, the contents of which are incorporated herein by reference in its entirety.

BACKGROUND

The present disclosure relates to an image processing technique which processes a tomographic image of an eye to be examined.

For an ophthalmologic photographing apparatus which can noninvasively capture a tomographic image of a predetermined part (for example, a fundus or an anterior ocular segment) of an eye to be examined, optical coherent tomography (OCT) using low coherent light is known (for example, refer to JP-A-2008-29467). In this ophthalmologic photographing apparatus, there are cases where a capturing position of a tomographic image is set on the basis of an instruction which is input by an examiner. For example, the examiner inputs an instruction for designating a capturing position of a tomographic image (that is, a cross sectional position at which measurement light is scanned) to the ophthalmologic photographing apparatus while observing, with a monitor, moving images obtained by photographing a front side of the eye.

SUMMARY

There is a case where a cross sectional position is set to have a predetermined angle relative to a specific direction of tissue of an eye to be examined so as to acquire or generate a tomographic image, thereby obtaining useful information. However, it is difficult to appropriately set the cross sectional position having the predetermined angle relative to the specific direction in the ophthalmologic photographing apparatus of the related art.

An object of the present disclosure is to provide an image processing apparatus capable of appropriately setting a cross sectional position for acquiring or generating a tomographic image of tissue of an eye, to have a predetermined angle relative to a specific direction of the tissue.

An aspect of the present disclosure provides the following arrangements:

An image processing apparatus configured to process a tomographic image of an object to be examined, comprising:
  a processor; and
  memory storing computer readable instructions, when executed by the processor, causing the image processing apparatus to:
  set a reference line, which is used as a reference for setting a cross sectional position, on a front image of the object, the cross sectional position being one of a position where a two-dimensional tomographic image is acquired from three-dimensional data of the object, and a position where measurement light for generating a tomographic image is scanned; and
  set the cross sectional position having a predetermined angle as an angle relative to the set reference line.

According to the technique of the present disclosure, it is possible to appropriately set a cross sectional position for acquiring or generating a tomographic image of tissue of an eye, at a predetermined angle with respect to a specific direction of the tissue.

BRIEF DESCRIPTION OF THE DRAWINGS

FIG. 4 is a diagram illustrating an example of a designated part diagnosis mode condition setting screen 15.

FIG. 5 is a diagram illustrating an example of a blood vessel diagnosis mode condition setting screen 16.

DESCRIPTION OF EXEMPLARY EMBODIMENTS

Hereinafter, an exemplary embodiment of the present disclosure will be described with reference to the drawings. In the following description, an axis direction of an eye E to be examined is set to a Z direction, a horizontal direction is set to an X direction, and a vertical direction is set to a Y direction. A surface direction of the fundus may be considered to be an XY direction.

Figure 1:
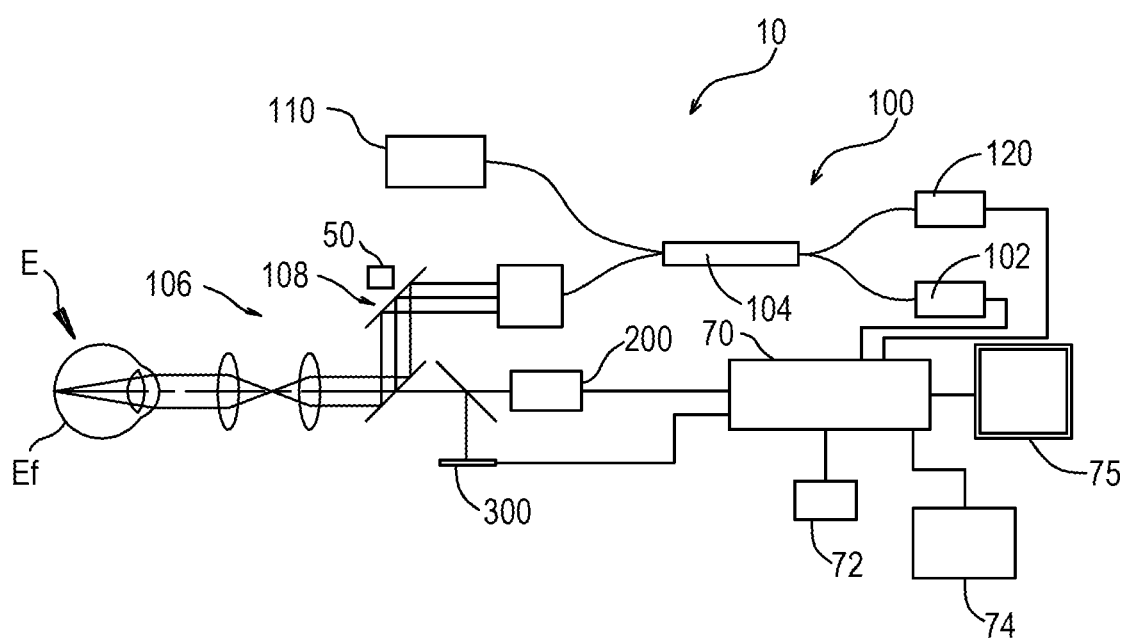
FIG. 1 is a diagram illustrating a schematic configuration of an ophthalmologic photographing apparatus 10.

With reference to FIG. 1, a schematic configuration of an ophthalmologic photographing apparatus 10 according to the present embodiment will be described. The ophthalmologic photographing apparatus (optical coherence tomographic apparatus) 10 according to the present embodiment includes an OCT optical system 100, an observation optical system 200, a fixation target projection unit 300, and a controller 70.

OCT Optical System

The OCT optical system 100 is an interference optical system which acquires a tomographic image of tissue (for example, the fundus Ef) of the eye E, and has a configuration of optical coherence tomography (OCT). Specifically, the OCT optical system 100 includes a measurement light source 102, a coupler (light splitter) 104, a measurement optical system 106, a reference optical system 110, and a detector (light receiving element) 120.

The measurement light source 102 emits light for acquiring a tomographic image. The coupler 104 splits the light emitted from the measurement light source 102 into measurement light (sample light) and reference light. The coupler 104 combines measurement light which is reflected by the fundus Ef and reference light generated by the reference optical system 110 and allows the detector 120 to receive the combined light.

The measurement optical system 106 guides the measurement light split by the coupler 104 to the fundus Ef of the eye E. Specifically, the measurement optical system 106 includes a light scanner 108 at a position which is substantially conjugate to the pupil. The measurement optical system 106 drives the light scanner 108 by using a driving mechanism 50 so as to scan the measurement light on the fundus Ef in a two-dimensional direction. As a result, a capturing position of a tomographic image on the fundus Ef is determined. In other words, a cross sectional position of the measurement light which is scanned by the light scanner 108 becomes a capturing position of a tomographic image. For example, a variety of devices which deflect light, such as a reflection mirror (a galvano mirror, a polygon mirror, or a resonant scanner) and an acoustic optical modulator (AOM) may be used as the light scanner 108.

The reference optical system 110 generates reference light. As described above, the reference light is combined with the reflected light of the measurement light from the fundus Ef. The reference optical system 110 may be of a Michelson type and of a Mach-Zehnder type. In the present embodiment, the reference optical system 110 reflects the light guided by the coupler 104 by using a reflection optical system which includes a reference mirror and the like. The reflected light is returned to the coupler 104 again as reference light. A configuration of the reference optical system 110 may be changed. For example, the reference optical system 110 may not reflect the light guided by the coupler 104 but may transmit the light through the detector 120 by using a transmission optical system such as an optical fiber.

The OCT optical system 100 changes an optical path length difference between the measurement light and the reference light. The OCT optical system 100 according to the present embodiment changes the optical path length difference by moving an optical member (specifically, the reference mirror) included in the reference optical system 110 in an optical axis direction. A configuration for changing an optical path length difference may be disposed in a measurement optical path of the measurement optical system 106.

The detector 120 detects an interference state of the measurement light and the reference light. In a case of Fourier domain OCT, a spectral intensity of interference light is detected by the detector 120, and a depth profile (an A scan signal) in a predetermined range is acquired through Fourier transform of the spectral intensity data. The ophthalmologic photographing apparatus 10 may employ a variety of OCT. For example, the ophthalmologic photographing apparatus 10 may employ any one of spectral-domain OCT (SD-OCT), swept-source OCT (SS-OCT), and time-domain OCT (TD-OCT).

Observation Optical System

The observation optical system 200 is provided so as to acquire a front image of tissue (the fundus Ef in the present embodiment) of the eye E. The observation optical system 200 according to the present embodiment has a configuration of a so-called scanning laser ophthalmoscope (SLO). More specifically, the observation optical system 200 includes a light scanner and a light receiving element (not illustrated). The light scanner scans measurement light (for example, infrared light) emitted from the light source on the fundus Ef in a two-dimensional direction. The light receiving element receives reflected light of the measurement light from the fundus Ef, via a confocal aperture disposed at a position which is substantially conjugate to the fundus Ef.

The observation optical system 200 may employ a configuration (a so-called fundus camera type configuration) of acquiring a front image such as a still image and a moving image by widely applying infrared light or the like. Further, the OCT optical system 100 may be also used as the observation optical system 200. In other words, the ophthalmologic photographing apparatus 10 may acquire a front image of the tissue by using data acquired by the OCT optical system 100, the data being used to generate a tomographic image. More specifically, the ophthalmologic photographing apparatus 10 may acquire a front image by using an integrated image of a three-dimensional tomographic image in a depth direction, an integrated value of spectrum data at respective positions in the XY direction, luminance data at respective positions in the XY direction in a specific depth direction, a retinal surface image, and the like.

The controller 70 described later may perform alignment (matching) between a front image acquired by the observation optical system 200 and an image (for example, a two-dimensional image from a front direction, obtained by integrating data of a three-dimensional image in the depth direction) acquired by the OCT optical system 100. In this case, the controller 70 may correlate the three-dimensional image with the front image so as to perform processes such as display and analysis on the correlated images.

Fixation Target Projection Unit

The fixation target projection unit 300 is provided so as to induce a visual line direction of the eye E. In the present embodiment, the fixation target projection unit 300 includes a visible light source which generates visible light, and changes a presentation position of an index shown by the visible light source. As a result, the visual line direction of the eye E is changed, and thus a photographing part of the fundus Ef is changed. For example, when a fixation target is presented from the same direction as a photographing optical axis, a central part of the fundus Ef becomes a photographing part. When the fixation target is presented over the photographing optical axis, an upper part of the fundus Ef becomes a photographing part. The fixation target projection unit 300 may employ various configurations. For example, a configuration may be employed in which a fixation position is adjusted by turning-on positions of LEDs which are arranged in a matrix. A configuration may be employed in which visible light is scanned using a light scanner. The fixation target projection unit 300 may be of an inner fixation lighting type in which a fixation target is displayed inside the device, and may be of an outer fixation lighting type in which a fixation target is displayed outside the device.

Controller

The controller 70 includes a CPU (processor), a RAM, a ROM, and the like. The CPU of the controller 70 controls the ophthalmologic photographing apparatus 10. The RAM temporarily stores various information. Various programs, initial values, and the like for controlling an operation of the ophthalmologic photographing apparatus 10 are stored in the ROM of the controller 70.

The controller 70 is electrically connected to a nonvolatile memory 72, an operation portion 74, a display portion 75, and the like. The nonvolatile memory 72 is a non-transitive storage medium which can hold storage content even if the supply of power is cut off. For example, a hard disk drive, a flash ROM, a USB memory attachable to and detachable from the ophthalmologic photographing apparatus 10, and the like, may be used as the nonvolatile memory 72. A photographing control program for controlling capturing of a front image and a tomographic image, performed by the ophthalmologic photographing apparatus 10, is stored in the nonvolatile memory 72. In addition, a two-dimensional tomographic image, a three-dimensional image, and a front image, which are captured, and various information regarding photographing such as information regarding a capturing position of a tomographic image, are stored in the nonvolatile memory 72. Various operation instructions are input to the operation portion 74 by an examiner.

The operation portion 74 outputs a signal corresponding to an input operation instruction to the controller 70. At least one of, for example, a mouse, a joystick, a keyboard, a touch panel, and the like may be used in the operation portion 74. The display portion 75 may be a display mounted in a main body of the ophthalmologic photographing apparatus 10, and may be a display connected to the main body. A display of a personal computer (hereinafter, referred to as a "PC") may be used. A plurality of displays may be used together. Various images including a tomographic image and a front image captured by the ophthalmologic photographing apparatus 10 are displayed on the display portion 75.

The controller 70 may be constituted by a plurality of controllers (that is, a plurality of processors). For example, the controller 70 of the ophthalmologic photographing apparatus 10 may be constituted by a setting controller provided in a PC and an operation controller which controls an operation of the OCT optical system 100 or the like. In this case, for example, the setting controller of the PC may set a capturing position of a tomographic image on the basis of an operation of the operation portion connected to the PC, and may instruct the operation controller to perform the setting content. The operation controller may control a photographing operation of each constituent element of the ophthalmologic photographing apparatus 10 on the basis of the instruction from the setting controller. A process of generating (acquiring) an image on the basis of a light receiving signal may be performed by either of the operation controller and the setting controller.

Figure 2:
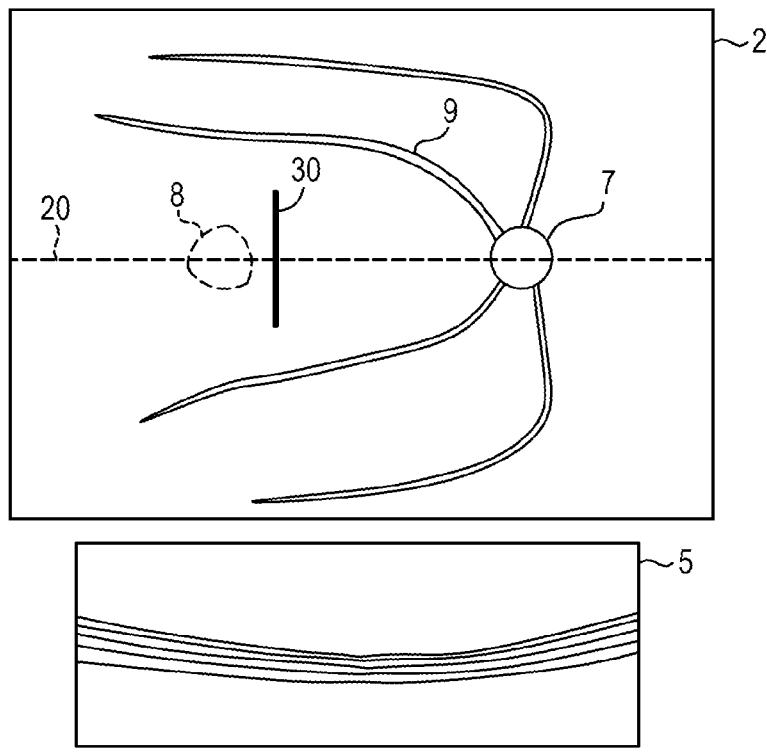
FIG. 2 is a diagram illustrating examples of a front image 2 and a tomographic image 5 displayed on a display portion 75.

With reference to FIG. 2, an outline of image capturing according to the present embodiment will be described. The ophthalmologic photographing apparatus 10 according to the present embodiment can appropriately set an acquisition position (that is, a cross sectional position of measurement light) of a tomographic image to have a predetermined angle relative to a specific direction of tissue (for example, the fundus Ef) of the eye E. There is a case where the cross sectional position is set to have the predetermined angle relative to the specific direction of the tissue, and thus a tomographic image useful for diagnosis is obtained. For example, in recent years, research results have been published in which the fundus Ef is divided using a line which passes through a papilla 7 and a macula 8 (refer to FIG. 2) as a boundary, and a relationship or the like between a structural change such as symmetry of retina thickness and a lesion is mentioned. If a cross sectional position is made to intersect the line passing through the papilla 7 and the macula 8, an examiner can easily judge symmetry of tissue in which the line serves as a boundary, from a tomographic image. In addition, in a case where a cross sectional position is made to intersect a blood vessel 9 (refer to FIG. 2), the examiner can easily judge a blood vessel diameter, a blood flow rate, a bloodstream, and the like from a tomographic image. Information useful to the examiner may be obtained by setting an angle of a cross sectional position depending on a lesion part. Further, useful information may be obtained by setting a cross sectional position parallel to a direction of tissue.

As illustrated in FIG. 2, the ophthalmologic photographing apparatus 10 according to the present embodiment sets a reference line 20 which is used as a reference for setting a cross sectional position 30, on a front image 2. The cross sectional position 30 having a predetermined angle as an angle relative to the set reference line 20 is set. Measurement light is scanned on tissue corresponding to the set cross sectional position 30, thereby obtaining a fundus image 5. Therefore, the ophthalmologic photographing apparatus 10 can appropriately set the cross sectional position 30 having a predetermined angle relative to a specific direction of the tissue. As a result, it is possible to easily obtain the tomographic image 5 useful for diagnosis.

A description will be made of photographing modes which can be executed by the ophthalmologic photographing apparatus 10 according to the present embodiment. The ophthalmologic photographing apparatus 10 can execute a "designated part diagnosis mode", a "blood vessel diagnosis mode", and a "normal mode". In the "designated part diagnosis mode", the linear reference line 20 is set at a part designated by the examiner, and an angle of the cross sectional position 30 is set on the basis of the set reference line 20. Therefore, the examiner just sets the reference line 20 in a desired direction at a desired part, and thus can easily set the cross sectional position 30 having a suitable angle. In the "blood vessel diagnosis mode", the reference line 20 is set along the blood vessel 9, and an angle of the cross sectional position 30 is set on the basis of the set reference line 20. Therefore, according to the "blood vessel diagnosis mode", the examiner can easily make a diagnosis related to the blood vessel 9. In the "normal mode", the cross sectional position 30 is set without setting the reference line 20. Hereinafter, a description of the "normal mode" will be made briefly.

Figure 3:
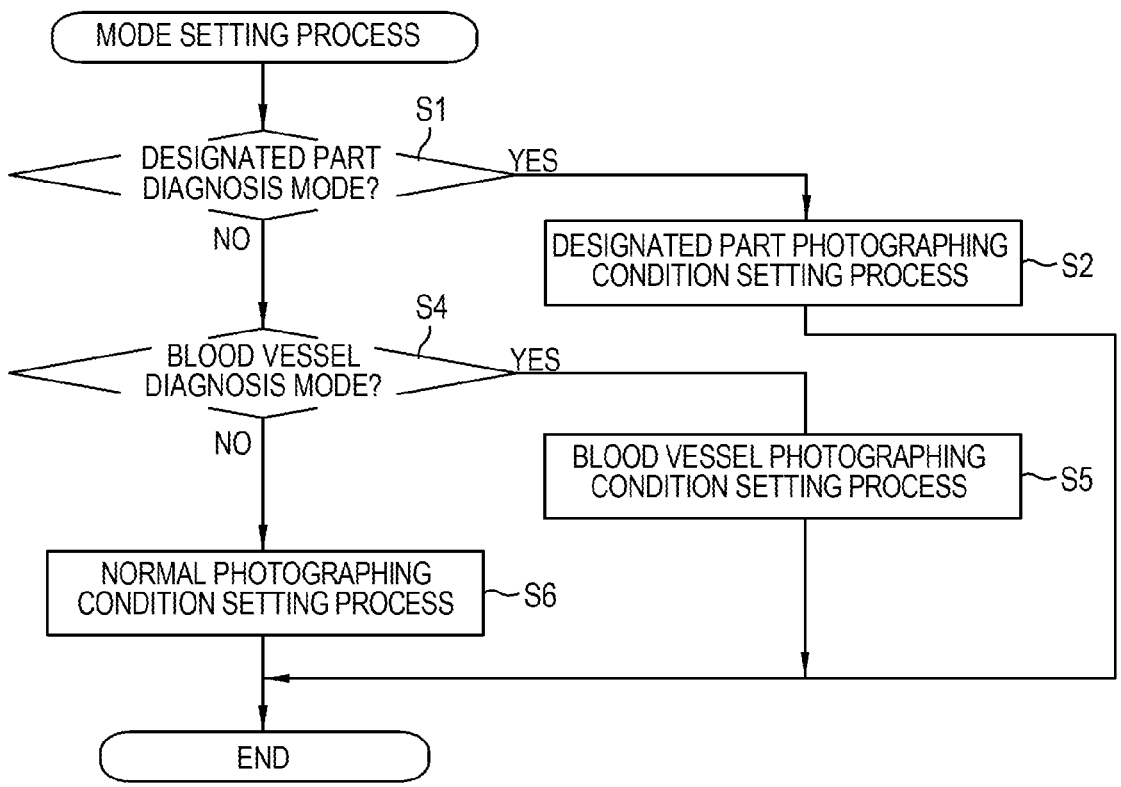
FIG. 3 is a flowchart illustrating a mode setting process performed by the ophthalmologic photographing apparatus 10.

With reference to FIGS. 3 to 5, a mode setting process performed by the controller 70 of the ophthalmologic photographing apparatus 10 will be described. In the mode setting process, any one of the "designated part diagnosis mode", the "blood vessel diagnosis mode", and the "normal mode" is selected by the examiner. In addition, a photographing condition for executing a selected mode is set on the basis of an instruction from the examiner. When an instruction for setting a photographing mode is input to the operation portion 74, the controller 70 performs the mode setting process illustrated in FIG. 3 according to the photographing control program stored in the nonvolatile memory 72.

In a case where the mode setting process starts, a selection screen (not illustrated) which allows the examiner to select a photographing mode is displayed on the display portion 75. The examiner operates the operation portion 74 (for example, a touch panel, a mouse, or the like) so as to input a mode selection instruction. If the selected mode is the "designated part diagnosis mode" (S1: YES), a designated part photographing condition setting process is performed (S2), and the mode setting process finishes. If the selected mode is not the "designated part diagnosis mode" (S1: NO) but the "blood vessel diagnosis mode" (S4: YES), a blood vessel photographing condition setting process is performed (S5), and the mode setting process finishes. If the "normal mode" is selected (S4: NO), a normal photographing condition setting process is performed (S6), and the process finishes.

As illustrated in FIG. 4, in the designated part photographing condition setting process (S2), a designated part photographing condition setting screen 15 is displayed on the display portion 75. In the designated part photographing condition setting screen 15, a reference line setting method selection item, a relative angle selection item, a cross sectional position setting method selection item, and a reference line photographing selection item are provided. The examiner operates the operation portion 74 so as to select any one of a plurality of options in each item. The controller 70 sets a photographing condition on the basis of the selection performed by the examiner.

The reference line setting method is a method of setting the reference line 20 on the front image 2. The reference line setting method according to the present embodiment includes options such as "papilla and macula automatic setting", "direct manual setting", and "passing point manual setting". In the option "papilla and macula automatic setting", the reference line 20 passing through the papilla 7 and the macula 8 is automatically set. In the option "direct manual setting", the examiner may manually set the reference line 20 having a desired angle at a desired position by moving a reference index which is displayed on the front image 2 in a superimposition manner. In the option "passing point manual setting", the examiner may set the reference line 20 passing through two passing points by manually setting the two passing points on the front image 2.

The relative angle is an angle of the cross sectional position 30 relative to the reference line 20. In the present embodiment, the examiner may select either of the options "perpendicular" and "arbitrary designation". If the examiner selects the option "perpendicular", the cross sectional position 30 perpendicular to the reference line 20 is set. If the examiner selects the option "arbitrary designation", a state in which an angle can be input occurs, and an input angle is set as the relative angle.

The cross sectional position setting method is a method of setting the cross sectional position 30 on the basis of the reference line 20. In the present embodiment, any one of options such as "manual", "number designation", and "space designation" may be selected. In the option "manual", the examiner may manually set a desired number of cross sectional positions 30 of which an angle relative to the reference line 20 is the relative angle, at desired positions. In the option "number designation", when the examiner designates the number of cross sectional positions 30, the cross sectional positions 30 of the designated number are set with equal spaces therebetween. In the option "space designation", a plurality of cross sectional positions are set between two end points on the reference line 20 with spaces therebetween designated by the examiner.

The reference line photographing indicates whether or not the cross sectional position 30 is set on the reference line 20. If an option of "YES" is selected, the cross sectional position 30 is also set on the reference line 20 in addition to the cross sectional position 30 intersecting the reference line 20. If an option of "NO" is selected, the cross sectional position 30 along the reference line 20 is not set.

As illustrated in FIG. 5, in the blood vessel photographing condition setting process (S5), a blood vessel photographing condition setting screen 16 is displayed on the display portion 75. In the blood vessel photographing condition setting screen 16, a relative angle selection item, a cross sectional position setting method selection item, and a display method selection item are provided. The relative angle selection item and the cross sectional position setting method selection item are the same as in the designated part photographing condition setting screen 15 (refer to FIG. 4). The display method is a method of displaying a tomographic image of the blood vessel 9. The examiner may select either of display methods of "moving image" and "still image".

With reference to FIGS. 6 to 11, a designated part photographing process performed by the controller 70 will be described. In the designated part photographing process, the fundus Ef is photographed in the "designated part diagnosis mode". When the "designated part diagnosis mode" is selected in the mode setting process (refer to FIG. 3), the controller 70 performs the designated part photographing process illustrated in FIG. 6 according to the photographing control program stored in the nonvolatile memory 72.

First, the observation optical system 200 (refer to FIG. 1) starts to capture a front image 2 of the fundus Ef so as to display moving images in real time on the display portion 75 (S11). If a reference line setting method selected by the examiner is the option "papilla and macula automatic setting" (S12: YES), a first reference line setting process is performed (S13), and the process proceeds to S18. If the option "direct manual setting" is selected (S12: NO, and S14: YES), a second reference line setting process is performed (S15), and the process proceeds to S18. If the option "passing point manual setting" is selected (S14: NO), a third reference line setting process is performed (S16), and the process proceeds to S18.

Figure 6:
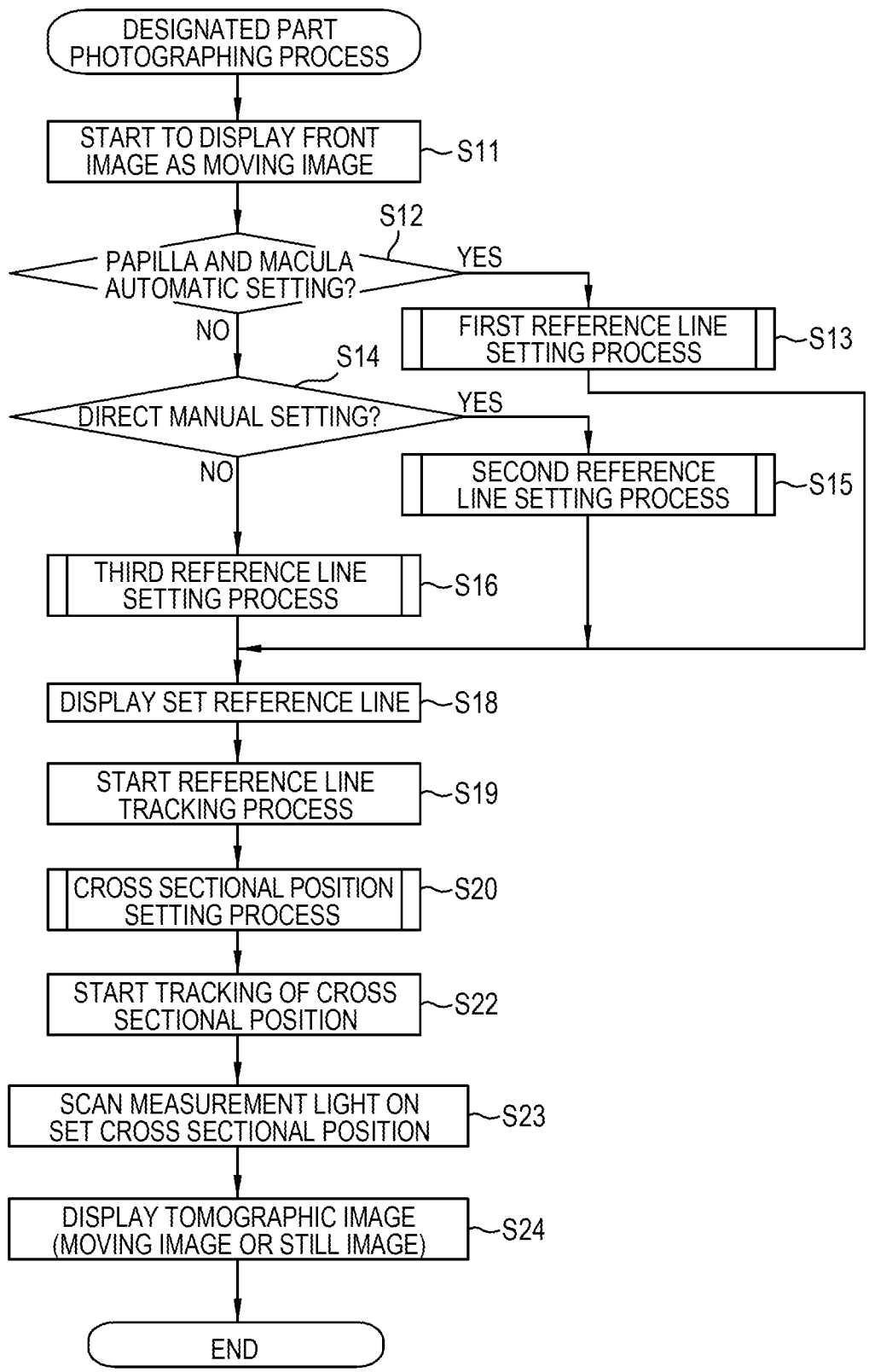
FIG. 6 is a flowchart illustrating a designated part photographing process performed by the ophthalmologic photographing apparatus 10.
Figure 7:
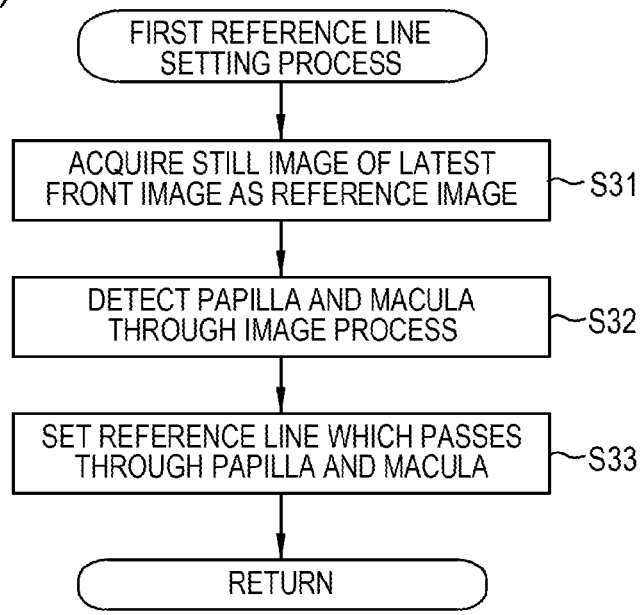
FIG. 7 is a flowchart illustrating a first reference line setting process which is performed in the designated part photographing process.

As illustrated in FIG. 7, in the first reference line setting process, the latest captured still image of the front image 2 is acquired as a reference image and is stored in the RAM (S31). A well-known image process is performed on the reference image, and thus a position of the papilla 7 and a position of the macula 8 (refer to FIG. 11) are detected (S32). As an algorithm for the image process, any one of various algorithms such as edge detection and Hough conversion algorithms may be used. Next, the linear reference line 20 which passes through both of the detected papilla 7 and macula 8 is set on the reference image (S33). The process returns to the designated part photographing process (refer to FIG. 6). Due to the above-described process, the reference line 20 which passes through the papilla 7 and the macula 8 is automatically set.

Figure 8:
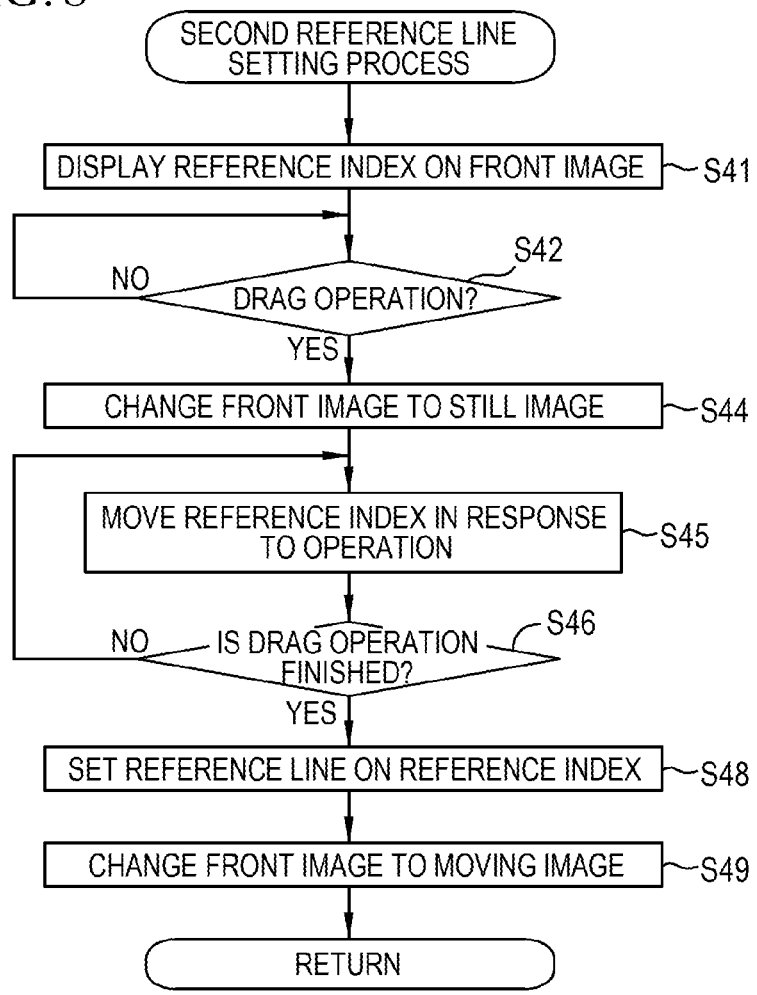
FIG. 8 is a flowchart illustrating a second reference line setting process which is performed in the designated part photographing process.

As illustrated in FIG. 8, in the second reference line setting process, a reference index which is used as an index for setting the reference line 20 is displayed on the front image 2 in a superimposition manner (S41). In the present embodiment, for example, the reference index is displayed by the broken line in the same manner as in the display aspect of the reference line 20 illustrated in FIG. 2. Next, it is determined whether or not a drag operation of the reference index is started by the examiner (S42). In the present embodiment, the examiner operates the mouse of the operation portion 74 so as to move a pointer to the reference index, and drags the pointer so as to move the reference index. However, a method of moving the reference index may be changed. A standby state occurs until the drag operation is performed (S42: NO). In addition, the controller 70 rotates the reference index displayed on the front image 2 on the basis of a predetermined operation (for example, a right click operation of the mouse, a rotation operation of the wheel, an operation on the keyboard, and the like) on the operation portion 74.

When the drag operation is started (S42: YES), the front image 2 which is currently displayed as moving images is stopped as the latest still image (S44). The reference index is moved on the front image 2 which is a still image in response to an operation on the operation portion 74 (S45). Therefore, the examiner can easily set the reference line 20 on the still image without being influenced by involuntary eye movement or the like during fixation. The process in S45 is continuously performed until the drag operation is finished (S46: NO). If the drag operation is finished (S46: YES), the reference line 20 is set on the moved reference index (S48). The front image 2 which is currently displayed as a still image is converted into a moving image (S49), and the process returns to the designated part photographing process (refer to FIG. 6). Due to the above-described process, the linear reference line 20 is directly manually set by the examiner. For example, in a case where the examiner wishes to set the reference line 20 illustrated in FIG. 11, the reference index may be moved to positions which pass through both of the papilla 7 and the macula 8.

Figure 9:
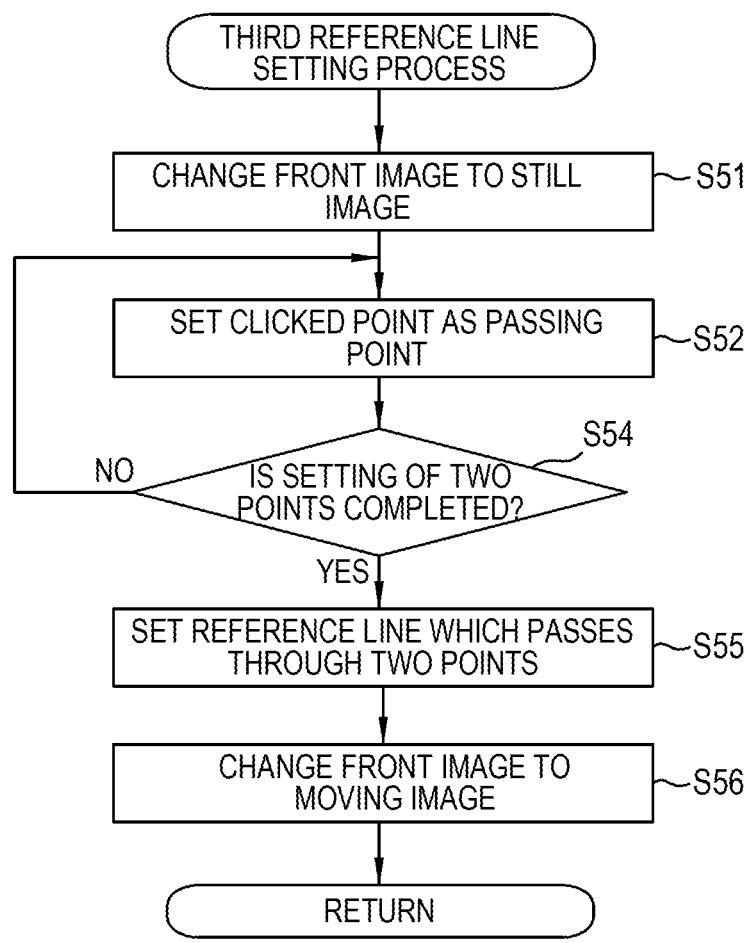
FIG. 9 is a flowchart illustrating a third reference line setting process which is performed in the designated part photographing process.

As illustrated in FIG. 9, in the third reference line setting process, the front image 2 which is currently displayed as a moving image is converted into the latest still image (S51). In the present embodiment, the examiner moves the pointer displayed on the front image 2 which is a still image with the mouse and performs a click operation, so as to designate positions of passing points of the reference line 20. When the click operation is performed, the controller 70 sets points designated by the click operation as the passing points (S52). The process in S52 is repeatedly performed until setting of two passing points is completed (S54: NO). If the setting of two passing points is completed (S54: YES), the reference line 20 which passes through both passing points is set (S55). The front image 2 which is currently displayed as a still image is converted into a moving image (S56), and the process returns to the designated part photographing process (refer to FIG. 6). Due to the above-described process, the examiner just manually sets two passing points at desired positions on the front image 2, so as to set the reference line 20. For example, in a case where the examiner wishes to set the reference line 20 illustrated in FIG. 11, a passing point may be set at each of the papilla 7 and the macula 8. In addition, the examiner can easily set the reference line 20 which crosses a lesion part or the like in a predetermined direction.

FIG. 6 will be continuously described. When the reference line 20 is set, the set reference line 20 is displayed on the front image 2 in a superimposition manner (S18). Subsequently, a reference line tracking process starts (S19). The reference line tracking process is a process of causing a position of the reference line 20 to track a correct position on the front image 2 which is currently displayed as a moving image. In the present embodiment, positional deviation of the front image 2 (that is, the latest front image 2) on which the reference line 20 has been set, relative to the front image 2 as a still image on which the reference line 20 was set, is detected through the above-described image process. Parameters of the detected positional deviation include a direction, a distance, and an angle. The controller 70 moves a position of the reference line 20 by a detected distance in a detected direction, and also rotates the reference line 20 by a detected angle. As a result, the reference line 20 tracks a correct position.

In addition, in a case of detecting positional deviation, the controller 70 is not required to directly compare all front images 2 which are continuously captured, with the front image 2 on which the reference line 20 was set. For example, the controller 70 may repeatedly detect positional deviation between the latest front image 2 and the front image 2 which is previously captured. Also in this method, it is possible to detect positional deviation of the latest front image 2 relative to the front image 2 on which the reference line 20 was set. Further, the controller 70 may change the front image 2 which is a comparison target every time a predetermined number of front images 2 as a still image are captured. Furthermore, the controller 70 may detect a relative position of the reference line 20 for a feature point on the front image 2, and may cause the reference line 20 to track the detected relative position so that the detected relative position is maintained.

Next, a cross sectional position setting process is performed (S20). In the cross sectional position setting process, the cross sectional position 30 of measurement light (that is, a capturing position of a tomographic image) is set on the basis of the reference line 20 set in S12 to S16.

Figure 10:
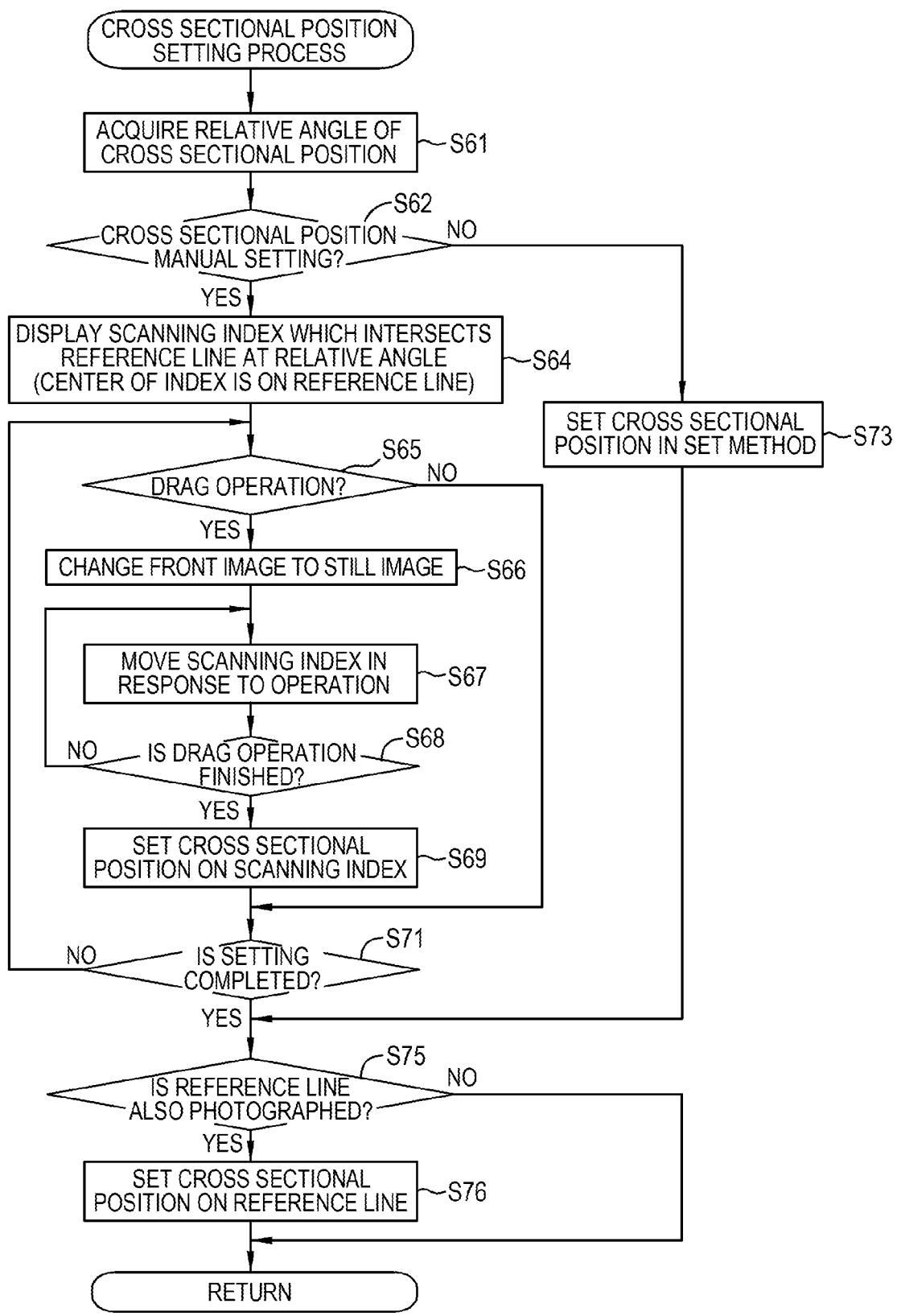
FIG. 10 is a flowchart illustrating a cross sectional position setting process which is performed in the designated part photographing process.

As illustrated in FIG. 10, when the cross sectional position setting process starts, the relative angle set in the mode setting process (refer to FIG. 3) is acquired (S61). As described above, the relative angle is an angle of the cross sectional position 30 relative to the reference line 20. In the present embodiment, the examiner may select the option "perpendicular" as the relative angle, and may designate a desired relative angle with the option "arbitrary designation". Next, it is determined whether or not a cross sectional position setting method which is set in the mode setting process is the option "manual" (S62).

If the option "manual" is set (S62: YES), first, a scanning index (for example, the index indicating the cross sectional position 30 in FIG. 2) which intersects the reference line 20 at a relative angle is displayed on the front image 2 in a superimposition manner (S64). The scanning index is preferably displayed in an aspect different from a display aspect of a reference index (for example, the index indicating the reference line 20 in FIG. 2). In this case, the examiner can easily differentiate both indexes from each other. In addition, the scanning index is displayed in a state in which the angle relative to the reference line 20 is fixed to the set relative angle and in a state in which the scanning index can be moved on the reference line 20. Further, the controller 70 preferably moves a center of the linear scanning index on the reference line 20. In this case, the reference line 20 is located at a center of a tomographic image. Therefore, the examiner can easily make a diagnosis centering on the reference line 20.

Next, it is determined whether or not a drag operation is started (S65). In the present embodiment, the examiner operates the mouse of the operation portion 74 so as to move a pointer to the scanning index, and drags the pointer so as to move the scanning index. In addition, the controller 70 moves the scanning index on the basis of a movement amount of a component parallel to a direction (in a case where the reference line 20 is a curve, a tangential direction of the reference line 20 at a position where the scanning index is displayed) in which the reference line 20 extends, among movement directions of the pointer. Therefore, the examiner can easily move the scanning index in a desired direction even if a direction of the reference line 20 is made not to accurately match a movement direction of the pointer. If the drag operation is not started (S65: NO), the process proceeds to determination in S71. If the drag operation is started (S65: YES), the front image 2 which is currently displayed as a moving image is converted into the latest still image (S66). The controller 70 moves the scanning index on the front image 2 which is a still image in response to the drag operation (S67). Thus, the examiner can easily move the scanning index to a desired position without being influenced by involuntary eye movement during fixation or the like. The process in S67 is continuously performed until the drag operation is finished (S68: NO).

Figure 11:
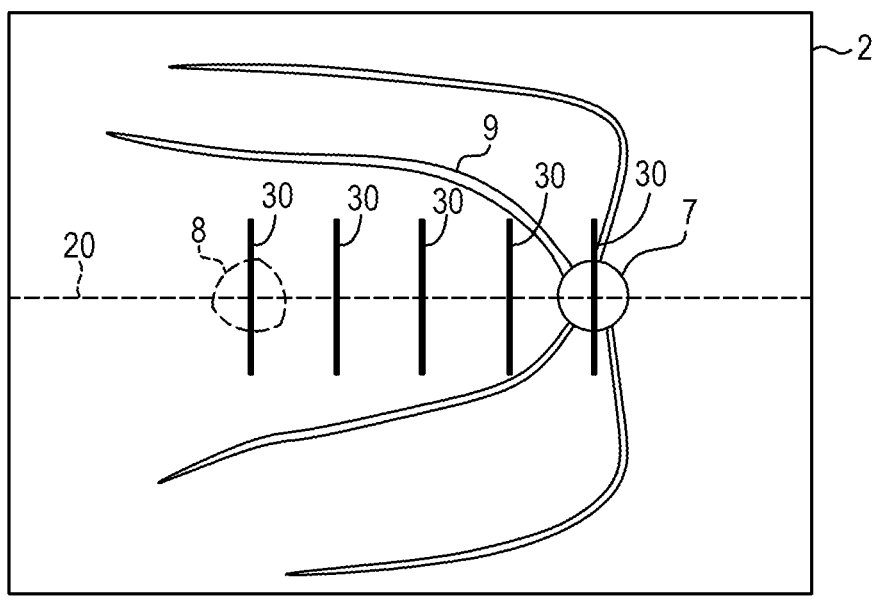
FIG. 11 is a diagram exemplifying a state in which five cross sectional positions 30 are set on the basis of a reference line 20 set in a designated part.

If the drag operation is finished (S68: YES), the cross sectional position 30 is set on the moved scanning index (S69). As illustrated in FIG. 11, the set cross sectional position 30 is displayed on the front image 2. Subsequently, it is determined whether or not an instruction for completing the setting of the cross sectional position 30 is input from the operation portion 74 (S71). For example, in a case of setting a plurality of cross sectional positions 30, the examiner may perform the next drag operation without inputting an instruction for completing the setting. If the instruction for completing the setting is not input (S71: NO), the process returns to the determination in S65. If the instruction for completing the setting is input (S71: YES), the process proceeds to determination in S75.

In addition, if a cross sectional position setting method set in the mode setting process (refer to FIGS. 3 to 5) is the option "number designation" or "space designation" (S62: NO), the cross sectional position 30 is set in the set method (S73), and the process proceeds to the determination in S75. Specifically, if the option "number designation" is set, the cross sectional positions 30 of the designated number are set between two end points on the reference line 20 (refer to FIG. 11). In the present embodiment, in a case where a plurality of cross sectional positions 30 are set by the option "number designation", centers of the respective cross sectional positions 30 are disposed with equal spaces therebetween. Accordingly, the examiner can make an efficient diagnosis related to tissue. In addition, if the option "space designation" is set, a plurality of cross sectional positions 30 are disposed with designated spaces therebetween between two end points on the reference line 20. Further, the space in the present embodiment is a space between centers of the cross sectional positions 30 in the same manner as in the option "number designation". However, the controller 70 may set a distance in the vertical direction between the respective cross sectional positions 30 to a space designated by the examiner. Furthermore, two end points on the reference line 20 may be set as appropriate. For example, in a case of the option "papilla and macula automatic setting", two end points may be respectively set in the center of the papilla 7 and the center of the macula 8. In a case of the option "passing point manual setting", two passing points may be set as end points without change. In a case of the option "direct manual setting", the controller 70 allows the examiner to designate two end points, or may automatically set end points.

Next, it is determined whether or not the reference line photographing is set to the option "YES" (S75). If the option "NO" is set (S75: NO), the process returns to the designated part photographing process (refer to FIG. 6). If the option "YES" is set (S75: YES), the cross sectional position 30 is also set on the reference line 20 (S76), and the process returns to the designated part photographing process.

FIG. 6 will be continuously described. If the cross sectional position setting process (S20) is finished, tracking of the cross sectional position 30 is started (S22). In the tracking process of the cross sectional position 30, in the same manner as in the above-described tracking process of the reference line 20, positional deviation of the latest front image 2 relative to the front image 2 which was acquired in the past is detected through an image process. The cross sectional position 30 is corrected on the basis of the detected positional deviation, thereby performing the tracking of the cross sectional position 30. Next, measurement light is scanned at the cross sectional position 30 of which the tracking is in progress (S23). As a result, a tomographic image 5 (refer to FIG. 2) at the set cross sectional position 30 is acquired. The captured tomographic image 5 is displayed as a moving image or a still image on the display portion 75 according to the setting (S24), and the process finishes. In a case where the tomographic image 5 is displayed as a moving image, the controller 70 may repeatedly scan the measurement light at the same cross sectional position 30 multiple times so that images are continuously displayed on the display portion 75.

Figure 12:
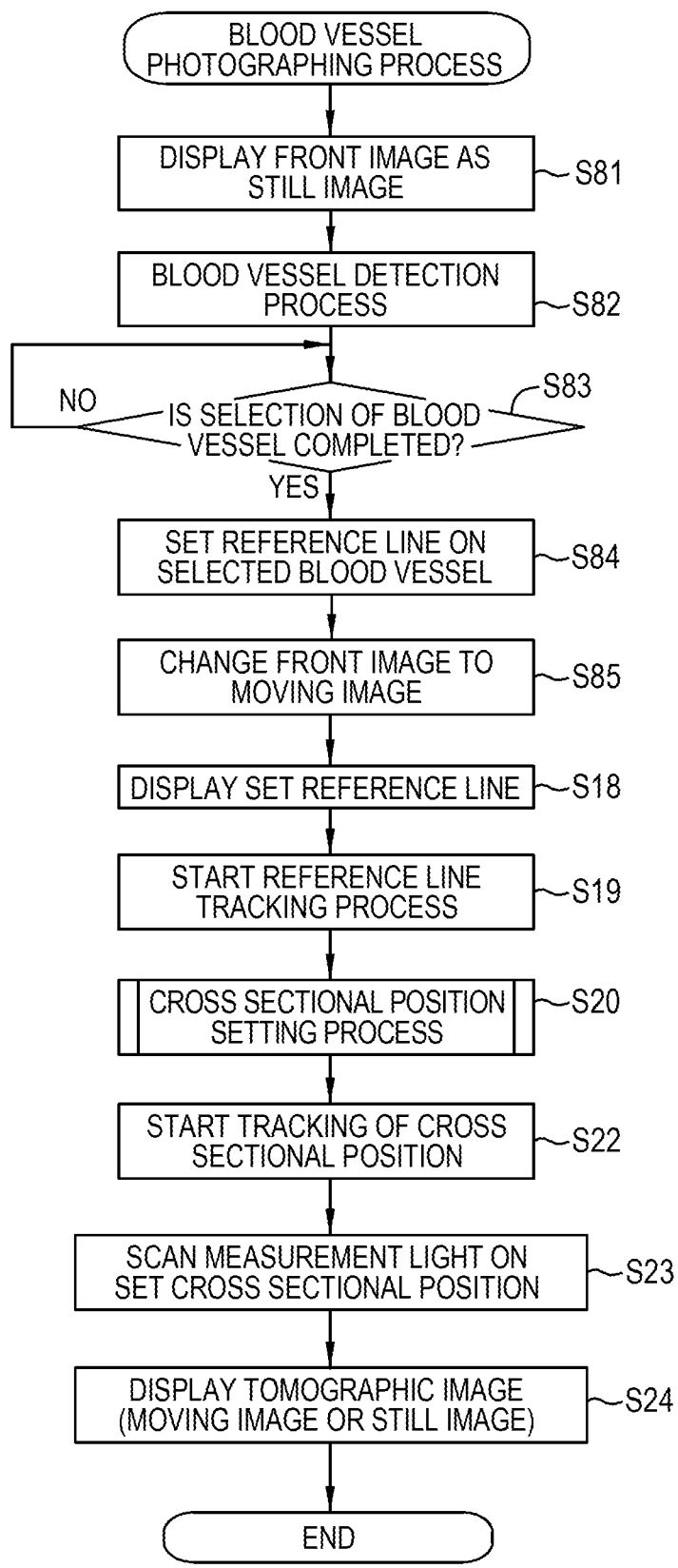
FIG. 12 is a flowchart illustrating a blood vessel photographing process performed by the ophthalmologic photographing apparatus 10.
Figure 13:
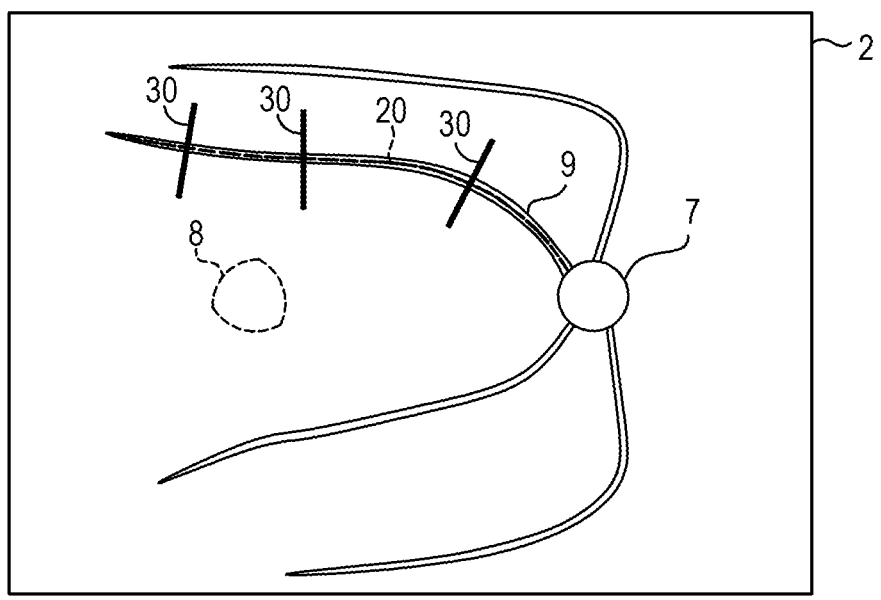
FIG. 13 is a diagram exemplifying a state in which three cross sectional positions 30 are set on the basis of a reference line 20 set in a blood vessel 9.

With reference to FIGS. 12 and 13, a blood vessel photographing process performed by the controller 70 will be described. In the blood vessel photographing process, the fundus Ef is photographed in the "blood vessel diagnosis mode". If the "blood vessel diagnosis mode" is selected in the mode setting process (refer to FIG. 3), the controller 70 performs a blood vessel photographing process illustrated in FIG. 12 according to the photographing control program stored in the nonvolatile memory 72. In addition, processes in S18 to S24 of FIG. 12 are the same as the processes in S18 to S24 of the above-described designated part photographing process. Therefore, a description of the processes in S18 to S24 will be omitted or briefly made.

First, the observation optical system 200 (refer to FIG. 1) captures the front image 2 of the fundus Ef, and the front image 2 which is a still image is displayed on the display portion 75 (S81). A blood vessel extraction process is performed on the displayed front image 2 by using a well-known blood vessel extraction algorithm (S82). In an example illustrated in FIG. 13, four blood vessels 9 which radically extend from the papilla 7 are extracted. The examiner operates the operation portion 74 so as to select the blood vessel 9 for diagnosis from one or a plurality of extracted blood vessels 9. The number of selected blood vessels 9 may be one or more. A standby state occurs until the selection is completed (S83: NO). If the selection of the blood vessel 9 is completed (S83: YES), the reference line 20 is set on the selected blood vessel 9 (that is, in the direction of the blood vessel 9) (S84). As illustrated in FIG. 13, for the most part, the blood vessel 9 is curved, and thus the reference line 20 is also curved. The front image 2 is converted from the still image to a moving image (S85).

Next, the reference line 20 set on the blood vessel 9 is displayed on the front image 2 (S18), and a tracking process of the reference line 20 starts (S19). The cross sectional position 30 is set by the cross sectional position setting process (refer to FIG. 10) (S20). FIG. 13 exemplifies a case where the cross sectional position 30 is manually set at three locations. In the manual setting, if the examiner performs an operation for moving a scanning index, the controller 70 moves the scanning index in a state in which an angle relative to the curved reference line 20 is maintained. Therefore, the examiner easily and reliably sets the cross sectional position 30 having a predetermined angle relative to a curved part (in this case, the blood vessel 9). Next, tracking of the cross sectional position 30 starts (S22), and measurement light is scanned on the cross sectional position 30 (S23). The captured tomographic image 5 is displayed as a moving image or a still image on the display portion 75 according to the setting (S24), and the process finishes.

In a case where the tomographic image 5 is set to be displayed as a moving image, the controller 70 continuously acquires a plurality of tomographic images 5 which are still images so as to generate the tomographic images 5 as moving images of tissue including the blood vessel 9. Therefore, the examiner can easily make various diagnoses related to the blood vessel 9.

As described above, the ophthalmologic photographing apparatus 10 according to the present embodiment sets an angle of the cross sectional position 30 to a predetermined angle relative to the reference line 20. Therefore, the examiner can appropriately set the cross sectional position 30 having a predetermined angle relative to a specific direction of tissue. Thus, the examiner can easily make an appropriate diagnosis.

The ophthalmologic photographing apparatus 10 according to the present embodiment sets the cross sectional position 30 intersecting the reference line 20 at a predetermined angle. Therefore, the examiner can easily and appropriately make a diagnosis related to the eye E by using the tomographic image 5 based on a direction of tissue. For example, the reference line 20 which passes through the papilla 7 and the macula 8 is set, and thus it is possible to easily confirm symmetry centering on the reference line 20 from the tomographic image 5. In addition, the reference line 20 may be set along the blood vessel 9, and thus the examiner can easily understand a blood vessel diameter, a blood flow rate, a bloodstream, and the like.

The ophthalmologic photographing apparatus 10 according to the present embodiment can set the cross sectional position 30 which intersects the reference line 20 so as to be perpendicular thereto. In this case, the examiner can more accurately understand symmetry of tissue with respect to the reference line 20. In addition, the ophthalmologic photographing apparatus 10 may allow the examiner to designate an angle (relative angle) of the cross sectional position 30 relative to the reference line 20. Therefore, the examiner can more freely and accurately cause the ophthalmologic photographing apparatus 10 to capture a desired tomographic image 5 so as to make a diagnosis. As an example, also in a case where the left and right eyes are compared with each other, in a case where eyes E of a plurality of subjects are compared with each other, and the like, the comparison can be performed using tomographic images 5 in which angles relative to a specific direction of tissue correctly match each other. More specifically, in a case where the left and right eyes are compared with each other, the ophthalmologic photographing apparatus 10 according to the present embodiment stores a relative angle of the cross sectional position 30 set when either of the eyes is photographed. Subsequently, when the other eye is photographed, the stored relative angle is horizontally reversed, and the cross sectional position 30 is set to have the reversed relative angle. Thus, the examiner can accurately compare the left eye with the right eye. Further, in a case where the left and right eyes are compared with each other, an angle of the reference line 20 relative to tissue may also be processed in the same manner as in a relative angle of the cross sectional position 30.

The ophthalmologic photographing apparatus 10 according to the present embodiment can set the reference line 20 by moving a reference index in response to an operation instruction from the examiner. In this case, the examiner can easily set a desired reference line 20 while looking at the front image 2 displayed on the display portion 75.

The ophthalmologic photographing apparatus 10 according to the present embodiment displays the scanning index on the front image 2 in a superimposition manner in an aspect different from a display aspect of the reference index indicating a position of the reference line 20. Next, the ophthalmologic photographing apparatus 10 may move the scanning index in response to an operation instruction from the examiner and may set the cross sectional position 30 on the moved scanning index in a state in which an angle relative to the reference line 20 is fixed. In this case, the examiner can easily differentiate the reference index from the scanning index so as to accurately set the cross sectional position 30. In addition, the examiner can freely and accurately set the cross sectional position 30 having a predetermined angle as an angle relative to the reference line 20, at a desired position. Further, the ophthalmologic photographing apparatus 10 displays the set reference line 20 on the front image 2 in a superimposition manner. Therefore, the examiner can easily and reliably check, on the front image 2, whether or not the reference line 20 is set an appropriate position.

The ophthalmologic photographing apparatus 10 according to the present embodiment displays the front image 2 as a still image on the display portion 75 while receiving an instruction input from the examiner, for setting at least the reference line 20. Therefore, even if the eye E is moved due to involuntary eye movement during fixation, breathing of a subject, or the like, the examiner can easily and reliably set the reference line 20 on the front still image 2.

The ophthalmologic photographing apparatus 10 according to the present embodiment can move (track) a position of the reference line 20 on the front image 2 on the basis of a capturing range of the front image 2. For example, even if a capturing range of the front image 2 varies due to involuntary eye movement during fixation after the reference line 20 is set, a position of the reference line 20 relative to captured tissue of the eye E is maintained. Therefore, even if the eye E is moved, the examiner is not required to set the reference line 20 again.

The ophthalmologic photographing apparatus 10 according to the present embodiment sets the cross sectional position 30 so that a central position of scanning is located on the reference line 20. In this case, the examiner can easily confirm the tomographic image 5 centering on the reference line 20. Particularly, in a case where the cross sectional position 30 is perpendicular to the reference line 20, the examiner can more accurately understand symmetry of tissue centering on the reference line 20.

The ophthalmologic photographing apparatus 10 according to the present embodiment can set the reference line 20 in (along) a direction of the blood vessel 9 in the fundus Ef of the eye E. In this case, the examiner can easily confirm the tomographic image 5 having the direction of the blood vessel 9 as a reference so as to make a diagnosis. Specifically, the ophthalmologic photographing apparatus 10 according to the present embodiment can detect the blood vessel 9 by using the blood vessel extraction algorithm, and can set the reference line 20 in a direction of the blood vessel 9. Therefore, the ophthalmologic photographing apparatus 10 can accurately set the reference line 20 in a direction of the blood vessel 9 without the examiner needing to perform many operations.

The ophthalmologic photographing apparatus 10 according to the present embodiment can continuously acquire a plurality of tomographic images 5 so as to generate the tomographic images 5 as moving images of tissue including the blood vessel 9. Therefore, the examiner can confirm the tissue including the blood vessel 9 by the moving images. Thus, the examiner can appropriately and accurately understand a blood flow state (for example, a blood flow rate and a bloodstream) of the blood vessel 9 with a simple operation.

The present invention is not limited to the above-described embodiment, and may have various modifications. The ophthalmologic photographing apparatus 10 according to the above-described embodiment captures the tomographic image 5 by using the OCT optical system 100. However, the present invention is not limited to the apparatus including the OCT optical system 100. In other words, the present invention is applicable to an ophthalmologic photographing apparatus as long as the ophthalmologic photographing apparatus can capture the tomographic image 5 and the front image 2.

In the above-described embodiment, a case of photographing the fundus Ef of the eye E has been exemplified and described. However, the present invention is also applicable to a case of capturing the tomographic image 5 of parts (for example, an anterior ocular segment) other than the fundus Ef. In addition, the present invention is also applicable to apparatuses which photograph objects (for example, internal organs, a semiconductor, and the like) other than the eye. More specifically, in a case or the like of checking symmetry of a manufactured semiconductor, if the reference line 20 is set so as to cross a center of a part whose symmetry is to be checked, an operator can easily carry out a useful inspection.

In the above-described embodiment, if the "designated part diagnosis mode" is selected, the linear reference line 20 is set, and if the "blood vessel diagnosis mode" is selected, the reference line 20 along the blood vessel 9 is set. However, an aspect of the reference line 20 is not limited thereto. For example, the ophthalmologic photographing apparatus 10 may set the reference line 20 with other shapes such as an arc shape and a polygonal shape. Also in this case, the cross sectional position 30 having a predetermined angle as an angle relative to the reference line 20 may be set.

The ophthalmologic photographing apparatus 10 according to the above-described embodiment sets the cross sectional position 30 which intersects the reference line 20 at a predetermined angle. Therefore, the examiner can easily understand the tomographic image 5 in a direction of which the tomographic image 5 intersects the reference line 20. However, the ophthalmologic photographing apparatus 10 may stipulate only an angle of the cross sectional position 30 relative to the reference line 20 without intersection between the reference line 20 and the cross sectional position 30. Also in this case, the examiner can appropriately set the cross sectional position 30 having a predetermined angle relative to a specific direction of tissue. Therefore, the ophthalmologic photographing apparatus 10 may set the cross sectional position 30 parallel to the reference line 20 or the like. For example, the ophthalmologic photographing apparatus 10 may perform scanning (and thus raster scanning) at a plurality of cross sectional positions 30 which are parallel to the reference line 20 and have different distances from the reference line 20, so as to acquire three-dimensional data or map data of an object to be examined. In this case, the examiner can make an appropriate diagnosis by using the data which is acquired through the scanning in the appropriate direction. In addition, in a case where the reference line 20 is a curve, the ophthalmologic photographing apparatus 10 may set the cross sectional position 30 in a tangential direction of the reference line 20. The cross sectional position 30 may be invariably set to be perpendicular to the reference line 20. Further, the ophthalmologic photographing apparatus 10 according to the above-described embodiment sets the cross sectional position 30 so that a central position of scanning is located on the reference line 20. Therefore, the examiner can easily confirm the tomographic image 5 centering on the reference line 20. However, the present invention can be realized even if a central position of scanning is not located on the reference line 20.

The ophthalmologic photographing apparatus 10 according to the above-described embodiment can set the reference line 20 in any method of "papilla and macula automatic setting", "direct manual setting", and "passing point manual setting". However, the ophthalmologic photographing apparatus 10 preferably performs at least one process of setting the reference line 20. In addition, in the above-described embodiment, a description has been made of a case of setting the reference line 20 which passes through both the papilla and the macula. However, a position where the reference line 20 is set may be changed. For example, the reference line 20 which passes through a lesion part and the papilla may be set. The reference line 20 which passes through a lesion part and the macula may be set. In a case where a lesion part can be identified through an image process, the reference line 20 which passes through the lesion part may be automatically set using the image process.

In the above-described embodiment, a photographing mode is first selected, and a process such as setting of the reference line 20 is performed on the basis of the selected mode. However, a setting method of the reference line 20 may be set and changed in the middle of the photographing. Similarly, in the above-described embodiment, a reference line setting method, a relative angle and cross sectional position setting method, reference line photographing, and a display method are set in advance, and then a process such as setting of the reference line 20 is performed (refer to FIGS. 4 and 5). However, timings for performing various settings may be changed as appropriate. For example, the ophthalmologic photographing apparatus 10 may set or change a relative angle after setting the reference line 20. The ophthalmologic photographing apparatus 10 may freely change a cross sectional position setting method in the cross sectional position setting process (refer to FIG. 10). The ophthalmologic photographing apparatus 10 may change a display method (a moving image or a still image) at any timing in response to an operation instruction from the examiner. In addition, the cross sectional position setting method may also be changed. For example, even in a case where the option "manual" is selected, the examiner may designate the number of cross sectional positions or a space therebetween.

A specific setting method of the reference line 20 may be changed as appropriate. For example, the ophthalmologic photographing apparatus 10 may select the reference line 20 without allowing the examiner to select either of the options "direct manual setting" and "passing point manual setting" in advance. In this modification example, the ophthalmologic photographing apparatus 10 may perform, for example, the second reference line setting process (refer to FIG. 8) when the reference index is dragged, and may perform the third reference line setting process (refer to FIG. 9) when a passing point is designated due to clicking. In addition, the ophthalmologic photographing apparatus 10 may set the reference line 20 based on an operation instruction from the examiner, in methods other than the options "direct manual setting" and "passing point manual setting". For example, the controller 70 may set one point designated through a click operation as a passing point of the reference index, and may set the reference line 20 by changing an angle or the like of the reference index under a condition that the reference index passes through the passing point.

In the ophthalmologic photographing apparatus 10 according to the above-described embodiment, the linear reference index and reference line 20 are displayed on the front image 2 so as to cross the entire display region of the display portion 75. Therefore, the examiner can accurately perform an operation while looking at an image even in a case where the reference line 20 is set to pass through two points which are spaced far apart from each other on the front image 2. However, the reference index and the reference line 20 may be lines with a specific length.

The ophthalmologic photographing apparatus 10 according to the above-described embodiment displays the set reference line 20 on the front image 2. Therefore, the examiner can easily check whether or not the reference line 20 is correctly set. However, the cross sectional position 30 may be set without displaying the reference line 20. In other words, the ophthalmologic photographing apparatus 10 may set the reference line 20 on the front image 2 which is internally acquired. In addition, when a display aspect of the reference index is different from a display aspect of the reference line 20, the examiner can more easily confirm setting content. Similarly, the scanning index and the set cross sectional position 30 may be displayed in different display aspects.

The ophthalmologic photographing apparatus 10 according to the above-described embodiment receives designation of a position of the reference line 20 on the front image 2 which is a still image. Therefore, the examiner can easily and reliably set the reference line 20 even in a case where the eye is moved. However, designation of a position of the reference line 20 on the front image 2 which is a moving image may be received. Also in this case, a process of tracking a position of the reference line 20 is performed after the reference line 20 is set, and thus it is possible to alleviate an operation burden on the examiner. In addition, the ophthalmologic photographing apparatus 10 may not only display a still image during setting of the reference line 20, but may also continuously display the still image during setting of the cross sectional position 30 which is subsequently performed. In the above-described embodiment, a case where a single reference line 20 is set has been exemplified. However, a plurality of reference lines 20 may be set on the front image 2. Further, the ophthalmologic photographing apparatus 10 may adjust the reference line 20 which is temporarily set, in response to an operation instruction from the examiner. An adjustment processing method may employ the same method as the above-described processing method in S45.

The ophthalmologic photographing apparatus 10 according to the above-described embodiment can automatically detect the blood vessel 9 and can set the reference line 20 along the detected blood vessel 9. Therefore, the examiner can accurately and easily set the reference line 20 on the blood vessel 9. However, a method of setting the reference line 20 on the blood vessel 9 may be changed. For example, the ophthalmologic photographing apparatus 10 may determine a trajectory of the pointer which is moved in response to an operation instruction from the examiner, as a shape of the blood vessel 9, and may set the reference line 20 on the trajectory. In addition, the ophthalmologic photographing apparatus 10 may set the reference line 20 along a trajectory which is drawn on a touch panel. Further, the ophthalmologic photographing apparatus 10 according to the above-described embodiment allows the examiner to select one or a plurality of blood vessels 9 on which the reference line 20 is to be set, in a case where a plurality of blood vessels 9 are automatically detected. Therefore, the examiner can easily make a diagnosis related to a desired blood vessel 9. However, the ophthalmologic photographing apparatus 10 may set the reference line 20 on all of the automatically detected blood vessels 9.

In a case where the set reference line 20 is not a single straight line (for example, a curve along the blood vessel 9), the ophthalmologic photographing apparatus 10 may set a plurality of cross sectional positions so that the cross sectional positions do not intersect each other. Specifically, the ophthalmologic photographing apparatus 10 may prevent intersection between the cross sectional positions by adjusting a space between positions of the plurality of adjacent cross sectional positions. The intersection may be prevented by adjusting a length of the cross sectional position. The intersection between the cross sectional positions is prevented, and thus the same part is not shown in a plurality of tomographic images, thereby increasing efficiency of diagnosis.

The ophthalmologic photographing apparatus 10 according to the above-described embodiment sets the reference line 20 before capturing a tomographic image, and sets the cross sectional position 30 which is a position where measurement light is scanned so that an angle relative to the set reference line 20 becomes a predetermined angle. However, it is also possible to improve convenience in a case of displaying a tomographic image at a predetermined cross sectional position from three-dimensional data of an object to be examined which has already been acquired, by changing "capturing" in the above-described embodiment to "display". In other words, in a case of displaying a tomographic image at a cross sectional position having a predetermined angle (for example, an angle at which symmetry of an object is easily confirmed) by using three-dimensional data of the object which has already been acquired, the case may be performed by modifying the above-described embodiment.

An embodiment of this modification example is exemplified. An image processing apparatus (for example, the ophthalmologic photographing apparatus 10, the PC, or the like) which processes a tomographic image preliminarily acquires three-dimensional data (three-dimensional image) of an object, obtained by performing raster scanning of measurement light. In a designated part "display" process which is a modification of the process of FIG. 6, a tomographic image at the set cross sectional position is acquired from the three-dimensional data instead of scanning of measurement light in S23. The acquired tomographic image is displayed in S24. In addition, in this modification example, the front image displayed in S11 may be a still image. The tracking (S18) of the reference line 20 and the tracking (S22) of the cross sectional position may not be performed. Further, other processes such as the cross sectional position setting process (refer to FIG. 10) may generally employ the processes exemplified in the above-described embodiment.

An image processing program which is executed by the image processing apparatus of this modification example may have the following configuration. "An image processing program is executed in an image processing apparatus which acquires a two-dimensional tomographic image of an object from three-dimensional data of the object, and is executed by a processor of the image processing apparatus so as to cause the image processing apparatus to perform: a three-dimensional data acquisition step of acquiring the three-dimensional data; a display control step of displaying a front image of the object on display means; an instruction reception step of receiving an input of an instruction from an examiner; a reference line setting step of setting a reference line which is used as a reference for setting a cross sectional position which is a position where the tomographic image is acquired, on the front image, in response to the instruction received in the instruction reception step; a cross sectional position setting step of setting the cross sectional position having a predetermined angle as an angle relative to the reference line set in the reference line setting step; and a tomographic image acquisition step of acquiring the tomographic image at the cross sectional position set in the cross sectional position setting step, from the three-dimensional data acquired in the three-dimensional data acquisition step."

In the above-described embodiment, the controller 70 provided in the ophthalmologic photographing apparatus 10 controls all operations of the ophthalmologic photographing apparatus 10. However, a device which controls some of the operations of the ophthalmologic photographing apparatus 10 may be used separately from the ophthalmologic photographing apparatus 10. For example, a PC is connected to the ophthalmologic photographing apparatus 10, and the PC may perform at least some of processes such as setting of the reference line 20 and setting of the cross sectional position 30. In this case, the PC may execute at least a part of the above-described photographing control program by using a processor.

What is claimed is:

1. An image processing apparatus configured to process a tomographic image of an object to be examined, comprising:
   a processor; and
   memory storing computer readable instructions, when executed by the processor, causing the image processing apparatus to:
   set a reference line, which is used as a reference for setting a cross sectional position, on a front image of the object, the cross sectional position being one of a position where a two-dimensional tomographic image is acquired from three-dimensional data of the object, and a position where measurement light for generating a tomographic image is scanned; and set the cross sectional position having a predetermined angle as an angle relative to the set reference line.

2. The image processing apparatus according to claim 1, wherein the computer readable instructions when executed by the processor causes the image processing apparatus to set the cross sectional position which intersects the reference line at a predetermined angle.

3. The image processing apparatus according to claim 2, wherein the computer readable instructions when executed by the processor causes the image processing apparatus to set the cross sectional position which perpendicularly intersects the reference line.

4. The image processing apparatus according to claim 2, wherein the computer readable instructions when executed by the processor causes the image processing apparatus to locate a center of the cross sectional position on the reference line.

5. The image processing apparatus according to claim 1, wherein the computer readable instructions when executed by the processor causes the image processing apparatus to receive designation of an angle of the cross sectional position relative to the reference line, and set the cross sectional position having the designated angle as an angle relative to the reference line.

6. The image processing apparatus according to claim 1, wherein the computer readable instructions when executed by the processor causes the image processing apparatus to set the cross sectional position which is parallel to the reference line.

7. The image processing apparatus according to claim 6, wherein the computer readable instructions when executed by the processor causes the image processing apparatus to control driving of scanning means for scanning the measurement light on the tissue of the object in such a manner that the measurement light is scanned on tissue corresponding to a plurality of cross sectional positions set to be parallel to the reference line.

8. The image processing apparatus according to claim 1, wherein the computer readable instructions when executed by the processor causes the image processing apparatus to:
acquire three-dimensional data of the object; and
acquire a tomographic image at the cross sectional position set in the front image based on the three-dimensional data.

9. The image processing apparatus according to claim 1, wherein the computer readable instructions when executed by the processor causes the image processing apparatus to control driving of scanning means for scanning the measurement light on the tissue of the object in such a manner that the measurement light is scanned on tissue corresponding to the cross sectional position set in the front image.

10. The image processing apparatus according to claim 1, wherein the computer readable instructions when executed by the processor causes the image processing apparatus to set at least one of the reference line and the cross sectional position in response to an instruction input from the examiner while the front image which is a still image is displayed on a display.

11. The image processing apparatus according to claim 1, wherein the computer readable instructions when executed by the processor causes the image processing apparatus to detect positional deviation of the front image after the reference line is set with respect to the front image when the reference line setting means sets the reference line through an image process, and track a position of the reference line after the reference line is set, to a correct position on the front image based on the result of the detected positional deviation.

12. The image processing apparatus according to claim 1, wherein the computer readable instructions when executed by the processor causes the image processing apparatus to perform an image process on the front image, and automatically set the reference line on the basis of a result of the image process.

13. The image processing apparatus according to claim 12, wherein the computer readable instructions when executed by the processor causes the image processing apparatus to detect positions of a papilla and a macula of an eye which is the object by performing an image process on the front image, and automatically set the linear reference line which passes through both of the detected papilla and macula.

14. The image processing apparatus according to claim 12, wherein the computer readable instructions when executed by the processor causes the image processing apparatus to perform a blood vessel detection process on the front image by using a blood vessel extraction algorithm, and set the reference line in a direction of the detected blood vessel.

15. The image processing apparatus according to claim 14, wherein the computer readable instructions when executed by the processor causes the image processing apparatus to:
generate the tomographic image as moving images of the tissue including the blood vessel, by continuously acquiring a plurality of tomographic images each of which is obtained by scanning the measurement light on the tissue of the object corresponding to a single cross sectional position.

16. A method of controlling an image processing apparatus configured to process a tomographic image of an object to be examined, the method comprising:
setting a reference line, which is used as a reference for setting a cross sectional position, on a front image of the object, the cross sectional position being a position where a two-dimensional tomographic image is acquired from three-dimensional data of the object, or a position where measurement light for generating a tomographic image is scanned; and
setting the cross sectional position having a predetermined angle as an angle relative to the set reference line.

17. A non-transitory computer readable recording medium storing computer readable instructions, when executed by the processor, causing an image processing apparatus to:
set a reference line, which is used as a reference for setting a cross sectional position, on a front image of the object, the cross sectional position being one of a position where a two-dimensional tomographic image is acquired from three-dimensional data of the object, and a position where measurement light for generating a tomographic image is scanned; and
set the cross sectional position having a predetermined angle as an angle relative to the set reference line.

* * * * *